United States Patent [19]

Brittain et al.

[11] Patent Number: 4,503,066

[45] Date of Patent: Mar. 5, 1985

[54] SPIRO-LINKED PYRROLIDINE-2,5-DIONES ACTIVE AS ENZYME ALDOSE REDUCTASE INHIBITORS

[75] Inventors: David R. Brittain, Macclesfield; Robin Wood, Hazel Grove, both of England

[73] Assignee: Imperial Chemical Industries PLC, London, England

[21] Appl. No.: 377,132

[22] Filed: May 11, 1982

[30] Foreign Application Priority Data

May 13, 1981 [GB]  United Kingdom ............... 8114625

[51] Int. Cl.$^3$ ................... A61K 31/41; C07D 491/107
[52] U.S. Cl. ......................... 514/409; 546/8;
546/10; 546/18; 546/65; 546/81; 546/153;
546/165; 548/302; 548/404; 548/410; 548/411;
549/23; 549/24; 549/26; 549/27; 549/28;
549/387; 549/390; 549/391; 549/407; 549/433
[58] Field of Search ................. 548/410, 404; 424/274

[56] References Cited

U.S. PATENT DOCUMENTS

| | | | |
|---|---|---|---|
| 3,185,696 | 5/1965 | Tien | 548/410 |
| 3,652,558 | 3/1972 | Lundsford et al. | 548/410 |
| 4,117,230 | 9/1978 | Sarges | 548/309 |
| 4,307,108 | 12/1981 | Belletire et al. | 548/410 |

FOREIGN PATENT DOCUMENTS 1133012  11/1968  United Kingdom .

OTHER PUBLICATIONS

Rice, et al., "Chemical Abstracts", vol. 74, 1971, col. 125384n.
Brittain, et al., "Chemical Abstracts", vol. 98, 1983, col. 98:143291e.
J. Heterocyclic Chemistry, 1971, 8, 155–156.
J. Medicinal Chemistry, 1981, 24, 47–53.

*Primary Examiner*—Glennon H. Hollrah
*Assistant Examiner*—James H. Turnipseed
*Attorney, Agent, or Firm*—Cushman, Darby & Cushman

[57] ABSTRACT

The invention provides various medical compositions for use in treating or preventing certain of the side effects of diabetes or galactosemia. The active ingredients are selected from a series of novel aldose reductase inhibitory spiro-linked pyrrolidine-2,5-diones of the general formula:

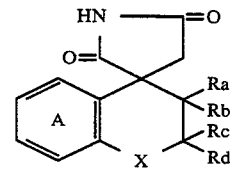

or a pharmaceutically acceptable salt, or a non-toxic, biodegradable precursor thereof. Processes for the production of these compounds are also provided. A particular compound suitable for use as an active ingredient is spiro[pyrrolidine-3,9'-xanthene]-2,5-dione.

5 Claims, No Drawings

SPIRO-LINKED PYRROLIDINE-2,5-DIONES ACTIVE AS ENZYME ALDOSE REDUCTASE INHIBITORS

This invention relates to novel medical compositions which contain as active ingredient a cyclic imide having the property of inhibiting the enzyme aldose reductase in vivo. More particularly, the cyclic imide is a spiro-linked pyrrolidine-2,5-dione, and the compositions are in general useful in the treatment or prophylaxis of those complications of protracted diabetes or galactosemia which are due at least in part to the undesirable tissue accumulation of sorbitol or galactitol, respectively.

The enzyme aldose reductase is responsible in man and other warm-blooded animals for the catalytic conversion of aldoses, for example glucose and galactose, to the corresponding alditols, for examle sorbitol and galactitol respectively. Alditols penetrate cell membranes poorly and, once formed, tend to be removed only by further metabolism. As a consequence, alditols tend to accumulate within cells where they are formed, for example in the lens, peripheral nerve tissue and kidney, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known that certain spiro-linked hydantoins (spiro-linked imidazolidine-2,5-diones) derived from various bicyclic ketones are inhibitors of the enzyme aldose reductase, for example the compounds of the general formula:

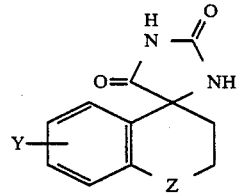

wherein Z is oxygen, sulphur, sulphinyl, sulphonyl, methylene or a direct bond, and Y stands for various optional substituents described by Sarges in U.S. patent Ser. No. 4,117,230. We have now discovered that certain spiro-linked succinimides (spiro-linked pyrrolidine-2,5-diones) of formula I below possess potent aldose reductase inhibitor properties, and this is the basis for our invention. This discovery is particularly surprising in view of the various chemical differences involved, for example in view of the significantly greater acidic properties of succinimides in comparison with hydantoins. Some structurally similar spiro-linked succinimides are known as chemical intermediates (UK patent specification No. 1133012) but have not previously been described as having pharmaceutically useful properties.

According to the invention there is provided a medical composition comprising as active ingredient a spiro-linked pyrrolidone-2,5-dione of the formula:

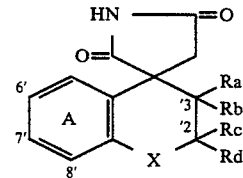

wherein:

(i) $R_a$, $R_b$, $R_c$ and $R_d$ are independently hydrogen or (1-6)alkyl; benzene ring A optionally bears 1 or 2 substituents independently selected from halogeno, (1-6C)alkyl, (1-6C)alkoxy, methylenedioxy, cyano and nitro substituents; and X is imino, (1-6C)alkylimino, phenylimino or benzylimino, in which the phenyl moiety optionally bears 1 or 2 halogeno, (1-6C)alkyl or (1-6C)alkoxy substituents; or (ii) $R_a$, $R_b$, $R_c$ and $R_d$ together with the adjacent ring carbon atoms 2' and 3' form a benzene or pyridine ring B; rings A and B optionally and independently bear 1 or 2 substituents as defined for ring A in (i) above; and X is oxygen, sulphur, sulphinyl, sulphonyl, methylene, (1-6C)alkylimino, phenylimino or benzylimino, in which the phenyl moiety is optionally substituted as defined for X in (i) above; or a salt with a base affording a pharmaceutically acceptable cation; or a non-toxic biodegradable precursor thereof; together with a pharmaceutically acceptable diluent or carrier.

Throughout this specification the terms $R_a$, $R_b$ et cetera are used to signify generic radicals and have no other significance.

The compounds of formula I all possess at least one asymmetric carbon atom, namely the spiro carbon atom of the pyrrolidine ring. The compounds of formula I therefore exist, and may be isolated, in one or more racemic and optically active forms. This invention encompasses the compounds of formula I in racemic form or in any optically-active form which possesses aldose reductase inhibitor properties, it being well known in the art how to prepare optically-active forms by resolution of the racemic form; or by synthesis from optically-active starting materials, and how to determine the aldose reductase inhibitory properties by the standard tests described hereinbelow.

The compositions of the invention may be in a form suitable for oral presentation, for example in the form of a tablet, capsule, granule, dispersible powder, syrup, elixir, emulsion, suspension or gel; for parenteral administration, for example in the form of a sterile injectable aqueous suspension or solution, or oily solution or suspension; for rectal administration, for example in the form of a suppository; or for topical administration to the eye, for example in the form of an ointment or sterile solution or gel buffered at an opthalmically acceptable pH, for example in the range pH 7.0–7.6.

The compositions may be manufactured by normal techniques of pharmacy using procedures, carriers and diluents well known in the art. In general oral compositions are preferred, but the exact form of composition and route of administration may vary depending on the host and aldose reductase containing tissue under treatment.

Tablets may be uncoated or they may be coated by known techniques to increase stability, to mask unpalatable taste, or to delay release of the active ingredient. They may in addition contain one or more sweetening, flavouring and colouring agents.

Capsules may be of hard gelatine and may contain the active ingredient alone, or in admixture with one or more solid non-toxic diluents or agents such as those mentioned above. Alternatively, capsules may be of soft gelatine wherein the active ingredient is mixed with an oily medium.

Syrups and elixirs are formulated with sweetening agents, for example sucrose or saccharin, and may also contain one or more conventional demulcents, flavouring and colouring agents.

Emulsions and suspensions may contain one or more conventional suspending agents, for example sodium carboxymethylcellulose or aluminium magnesium silicate, and dispersing and wetting agents, for example, a polysorbate, together with one or more conventional diluents, for example water, ethanol, glycerol, propylene glycol, polyethylene glycol, or an edible vegetable or mineral oil.

Gels may contain one or more conventional gelling agents, for example animal and vegetable fats, waxes, cellulose derivatives, silicones or polyethylene glycols.

Dispersible powders and granules which are suitable for the extemporaneous preparation of an aqueous suspension or solution may contain one or more conventional dispersing, suspending or wetting agents, buffering agents, or preservatives.

Compositions intended for parenteral or topical administration to the eye may be sterilised by conventional procedures.

Solutions for topical administration to the eye, for example in the treatment of diabetic cataracts, may contain one or more conventional buffers, for example boric acid, sodium or potassium carbonate, bicarbonate, acetate or borate; gelling or thickening agents, for example dextran, glycerol, cellulose derivatives or polyethylene glycol; or other conventional excipients well known in the art for use in the preparation of ophthalmic compositions. Similarly, ointments for topical administration to the eye may contain conventional excipients such as soft paraffin together with emulsifying and or thickening agents such as sorbitan monostearate.

Suppositories for administration of the active ingredient per rectum may be prepared by mixing the active ingredient with one or more conventional non-irritant excipients which are solid at ordinary temperatures but liquid at rectal temperature and which will thus melt in the body, releasing the active ingredient.

All the pharmaceutical compositions may be conveniently formulated together with a conventional antioxidant, for example sodium metabisulphite, and/or a preservative, for example methyl or propyl p-hydroxybenzoate.

Dosage unit forms of a composition of the invention, for example tablets, capsules or suppositories will in general contain 10-500 mg. of active ingredient, depending on the form involved.

Solutions and ointments for topical administration to the eye will in general contain 0.02-2.0% by weight of active ingredient.

A particular value for Ra, Rb, Rc or Rd when it is (1-6C)alkyl is, for example, methyl or ethyl.

Particular values for substituents which may be present on rings A or B are by way of example:
for halogeno, fluoro, chloro, bromo or iodo;
for (1-6C)alkyl, methyl or ethyl; and
for (1-6C)alkoxy, methoxy or ethoxy.

A particular value for X when it is (1-6C)alkylimino is, for example, methylimino or butylimino, and particular values for the substituents which may be present on the phenyl moiety when X is benzylimino or phenylimino are, for example, fluoro, chloro, bromo, methyl or methoxy.

In this specification the term non-toxic, biodegradable precursor includes derivatives of the compounds of formula I defined above in which the imino hydrogen atom in the pyrrolidine ring is replaced by a biodegradable protecting group known in the art, which group is, not inherently toxic and which is capable of relatively facile removal in vivo (for example by enzymic hydrolysis) to liberate the compound of formula I in sufficient quantity to inhibit the enzyme aldose reductase and without giving rise to pharmacologically unacceptable by-products. Examples of suitable groups for inclusion in biodegradable precursors of compounds of formula I include alkoxycarbonyl, aralkoxycarbonyl, alkoxyoxalyl and 1-(alkoxycarbonyloxy)alkyl groups, such as ethoxycarbonyl, t-butyloxycarbonyl, benzyloxycarbonyl, ethoxyoxalyl, methoxyoxalyl and pivaloyloxymethyl groups. The biodegradable precursors are not in general themselves inhibitors of the enzyme aldose reductase, but are active in vivo by virtue by removal of the biodegradable protecting radical. It will be apparent therefore that by suitable choice of biodegradable protecting groups (for example based on their generally known rates of enzymic degradation) it is possible to produce biodegradable precursors of compounds of formula I whose bioabsorption and distribution properties differ from those of the compounds of formula I.

Specific values for ring A or B of particular interest are, for example, when it is an unsubstituted pyridine or benzene moiety, or a pyridine or benzene moiety bearing a fluoro, chloro, bromo, methyl, methoxy, methylenedioxy, cyano or nitro substituent in the 6'-, 7'- or 8'-position. Further, when Ra, Rb, Rc and Rd together with the adjacent ring carbon atoms 2' and 3' constitute a benzene or pyridine ring B, it is generally preferred that taken together rings A and B bear no more than 3 substituents.

A preferred group of active ingredients comprises those compounds of formula I wherein Ra, Rb, Rc and Rd, together with the adjacent ring carbon atoms 2' and 3', form a benzene or pyridine ring; ring A is a benzene moiety optionally bearing a halogeno substituent selected from chloro, bromo and fluoro, at the 6'-, 7'- or 8'-position, and X is oxygen, sulphur, sulphinyl, sulphonyl or (1-6C)alkylimino; together with the pharmaceutically acceptable salts and the non-toxic, biodegradable precursors thereof.

Particular salts with bases affording pharmaceutically acceptable cations are, for example, alkali metal or alkaline earth metal salts, such as sodium potassium, calcium or magnesium salts, aluminium or ammonium salts or salts with organic bases, such as triethanolamine.

The invention also provides a novel spiro-linked pyrrolidine-2,5-dione of the formula:

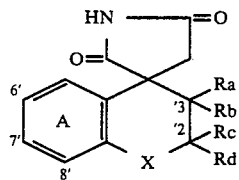

wherein Ra, Rb, Rc, Rd, X and benzene ring A have the meanings defined hereinabove; or a salt with a base affording a pharmaceutically acceptable cation; or a non-toxic, biodegradable precursor thereof.

Particular values for Ra, Rb, Rc, Rd, X and rings A and B are as defined hereinbefore.

A specific group of novel compounds of the invention which is preferred is comprised by those compounds of the formula:

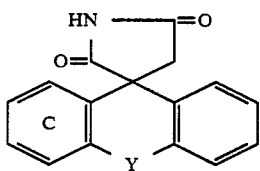

wherein benzene ring C optionally bears a halogeno, (1–4C)alkyl or (1–4C)alkoxy substituent; and Y is oxygen, sulphur or (1–6C)alkylimino; or a salt thereof; or a nontoxic biodegradable precursor thereof.

Particular values for substituents on benzene ring C are, for example, methyl, methoxy, fluoro, chloro and bromo substituents.

A compound of particular interest is, for example spiro[pyrrolidine-3,9'-xanthene]-2,5-dione, or a pharmaceutically acceptable salt thereof with a base affording a pharmaceutically acceptable cation.

The novel compounds of formula I may be obtained by any process known in the art for the manufacture of structurally analogous compounds. Such processes are provided as a further feature of the invention and are illustrated by the following procedures in which, unless otherwise stated, Ra, Rb, Rc, Rd, X and rings A and B have any of the above mentioned values:

(a) Decarboxylating an acid of the formula:

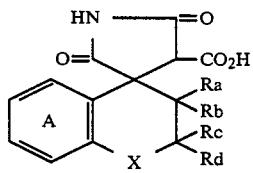

under the influence of heat.

The decarboxylation may be carried out at a temperature in the range, for example, 60°–200° and a suitable solvent or diluent, for example acetic acid diethanolamine or quinoline (optionally together with copper powder) may conveniently be present.

The starting materials of formula III are conveniently generated in situ by hydrolysis of the corresponding ester or nitrile of the formula:

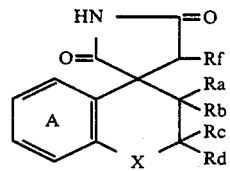

wherein Rf is alkoxycarbonyl (such as methoxycarbonyl), ethoxycarbonyl or t-butoxycarbonyl), aralkoxycarbonyl (such as benzyloxycarbonyl), cyano or carbamoyl. The hydrolysis may be carried out using conventional acid or base catalysed conditions, and at a temperature in the range, for example, 40°–100° C. When base catalysis is used the acid of formula III must be generated from the salt first obtained, by acidification with a mineral acid such as hydrochloric acid. When acid catalysis is used, the acid of formula III may undergo spontaneous decarboxylation to generate the compound of formula I.

When Rf is an (α,α-dibranched)alkoxycarbonyl group, such as t-butoxycarbonyl, the acid of formula III may be generated by thermolysis at a temperature in the range, for example, 120°–180° C., preferably in the absence of solvent or diluent and under reduced pressure. Under these conditions the acid of formula III undergoes decarboxylation to the compound of formula I.

When Rf is an aralkoxycarbonyl group, such as benzyloxycarbonyl, the acid of formula III may also be formed by conventional hydrogenolysis, for example using hydrogen at atmospheric pressure in a solvent, such as ethanol or aqueous ethanol, using a palladium based catalyst.

Particularly convenient conditions for the in situ formation and subsequent decarboxylation of an acid of formula III are provided by heating a compound of formula IV defined above in a (2–6C)alkanoic acid, such as acetic or propionic acid, in the presence of an inorganic acid, such as hydrogen chloride or hydrogen bromide, and at a temperature in the range for example, 100°–150° C. This process is included as a further feature of the invention.

The starting materials of formula IV may be obtained by cyclisation of a bifunctional derivative of the formula:

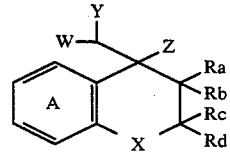

wherein one of W, Y and Z is cyano or carbamoyl and the other two are independently selected from cyano, carbamoyl, alkoxycarbonyl (such as methoxycarbonyl or ethoxycarbonyl) and aralkoxycarbonyl (such as benzyloxycarbonyl). A preferred value for Y and Z is, for example cyano and for W is, for example, methoxycarbonyl.

The cyclisation is normally carried out in the presence of an acid catalyst, for example a hydrogen halide, sulphuric acid or polyphosphoric acid, in a suitable solvent or diluent, for example a (2–6C)alkanoic acid, such as acetic or propionic acid, and at a temperature in the range 20° to 120° C. In some cases, if higher temperatures are employed, cyclisation of V to the compound of formula IV, hydrolysis to the acid of formula III, and decarboxylation to the compound of formula I, may occur simultaneously in situ.

The starting materials of formula V may be obtained by conventional procedures of organic chemistry. For example, those compounds wherein Z is cyano may be obtained by addition of cyanide to an unsaturated compound of the formula:

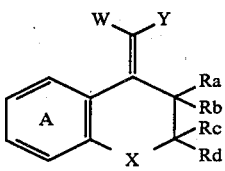

or a geometric isomer thereof, for example by reaction with potassium cyanide in methanol at a temperature of 10° to 50° C. The compounds of formula VI may themselves be obtained by reaction of compound of the formula W.CH$_2$Y with a ketone of the formula:

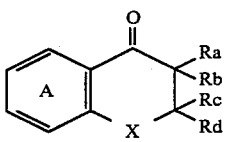

preferably in the presence of a base catalyst such as piperidine or ammonium acetate as illustrated in the accompanying Examples.

(b) Reacting a diacid of the formula:

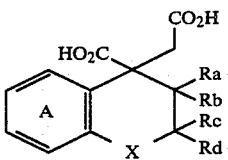

or an anhydride thereof with ammonia.

The starting diacids may be obtained, for example, by acid or base catalysed hydrolysis of the corresponding compound of formula V wherein Y and Z are cyano and W is methoxycarbonyl or ethoxycarbonyl, for example using aqueous hydrochloric acid at a temperature in the range 40° to 80° C. In some cases the diacids may cyclise to give the corresponding anhydrides. Alternatively, the anhydrides may be formed from the diacids by dehydration, for example by heating under reflux with acetic anhydride.

The process (b) is generally performed at an elevated temperature, for example in the range 150°–220° C. and may proceed through an intermediate amide of the formula:

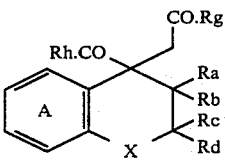

wherein one of Rg and Rh is amino and the other is hydroxy, which may also be used as starting material for the process. The ammonia is conveniently provided as a concentrated aqueous solution.

The non-toxic, biodegradable precursors of the compounds of formula I may be obtained by known acylation or alkylation procedures for the introduction of the necessary biodegradable protecting radicals. Examples of suitable acylating or alkylating reagents are, for example, alkoxycarbonyl, aralkoxycarbonyl, alkoxyoxalyl and 1-(alkoxycarbonyl)alkyl halides, such as methoxycarbonyl, t-butyloxycarbonyl, benzyloxycarbonyl, ethoxyoxalyl, methoxyoxalyl and pivaloyloxymethyl chloride. The reaction may be performed under conventional N-acylation/alkylation conditions, for example in the presence of a base such as potassium carbonate, or using the lithium, sodium or potassium salt of the compound of formula I and in a suitable solvent or diluent, such as 1,2-dimethoxyethane, di-n-butyl ether or diethyl ether, at a temperature in the range, for example, 10° to 80° C.

Whereafter when a pharmaceutically acceptable salt is required, a compound of formula I in free base form is reacted with a base affording a pharmaceutically acceptable cation, using a conventional procedure well known in the art.

Further, when an optically active form of a compound of formula I is required, a racemic form of the said compound may be reacted with an optically-active form of a suitable organic base, for example brucine, coniine, 2-pipecoline or an N,N,N-trialkyl-(1-phenylethyl)ammonium hydroxide such as N,N,N-trimethyl-(1-phenylethyl)ammonium hydroxide followed by conventional separation of the diastereoisomeric mixture of salts or complexes thus obtained, for example by fractional crystallisation from a suitable solvent, for example a (1–4C)alkanol, whereafter the optically-active form of the said compound may be liberated by treatment with acid using a conventional procedure, for example using an aqueous mineral acid such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2–4 hours from the final dose the animals are killed and the sciatic serves are removed and assessed for residual sorbitol levels as described above.

Preferred compounds in either of these tests reduce residual sorbitol levels to levels which are similar to those of normal, undosed rats. However, in general the compounds of formula I produce significant inhibition of the enzyme aldose reductase at an oral dose of 100 mg/kg or much less with no overt toxicity or other adverse effects at the active dose.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this tèst the compounds of formula I in general show significant inhibition of the enzyme aldose reductase at a concentration of about $10^{-6}$M or much less.

When a compound of the invention is used to produce an effect on the enzyme aldose reductase in warm-blooded animals, it may be administered primarily orally at a daily dose of 1.0 to 25 mg./kg. It is envisaged that in man a total daily dose in the range 20 to 750 mg. per man will be administered, given in divided doses if necessary.

Topical formulations may be administered to the eye of an animal, for example man or dogs, requiring treatment for diabetic cataracts or retinopathy in a conventional manner, for example using a drop or eye-wash topical formulation.

The invention also provides a method for inhibiting aldose reductase in an animal requiring such treatment which method comprises administering to said animal an aldose reductase inhibitory amount of a compound of formula I as defined anywhere hereinbefore, or a pharmaceutically acceptable salt thereof.

The compositions of the invention may also contain one or more other agents which may or are known to have a useful effect in the treatment of diabetes or galactosemia, for example a hypoglycaemic agent such as tolbutamide, chlorpropamide, or glybenclamide.

The invention will now be illustrated in the following non-limiting Examples in which, unless otherwise stated:

(i) all evaporations were carried out by rotary evaporation in vacuo;

(ii) all operations were carried out at room temperature, that is in the range 18°-26° C.;

(iii) petroleum ether (b.p. 60°-80° C.) is referred to as "petrol 60-80", and other petroleum ether fractions accordingly; and (iv) yields (where given) are for illustration only and are not to be construed as the maximum attainable.

EXAMPLE 1

9-Carboxyxanthene-9-acetic acid (1.2 g.) was heated under reflux in acetic anhydride (20 ml.) for 90 minutes. The mixture was evaporated and the residue was suspended in toluene (100 ml.). The mixture was azeotroped under vacuum and evaporated. This procedure was repeated. The dry residue obtained [9'-spiroxanthene-succinic anhydride] was dissolved in 1,2-dimethoxyethane (25 ml.) and ammonia solution (5 ml., density 0.880) was added. The solution obtained was heated to 180° C. and volatile material was allowed to distil out during 40 minutes. The residue was cooled to 40°-25° C., whereupon a solid crystallised. This solid was recrystallised from 2-propanol/petrol 60-80 to give spiro[pyrrolidine-3,9'-xanthene]-2,5-dione (0.7 g.), m.p. 226°-228° C.

The starting material was obtained as follows: Ethyl-(α-cyano-Δ9,α-xantheneacetate (8.7 g.) (Hafez et alia, J.Org.Chem, 1961, 26, 3988-3991) was dissolved in ethanol (120 ml.). Potassium cyanide (2.0 g.) was added and the solution was heated under reflux for four hours. The solvent was evaporated and concentrated hydrochloric acid (120 ml.) was added to the residue. The resulting solution was heated under reflux for 16 hours, cooled, diluted with water (200 ml.) and then extracted with ethyl acetate (200 ml.). The extract was washed with water (3×150 ml.) and then itself extracted with 2M sodium hydroxide (3×100 ml.). The alkaline extracts were combined, washed with ether (3×150 ml.) and then acidified with concentrated hydrochloric acid. The solid which formed was collected by filtration, washed with water, air-dried and recrystallised from 2-propanol/petrol 60-80 to give 9-carboxyxanthene-9-acetic acid (1.4 g.).

EXAMPLE 2 (ALL PARTS BY WEIGHT)

A mixture of spiro[pyrrolidine-3,9'-xanthene]-2,5-dione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 or 100. mg. of active ingredient and suitable for oral administration for therapeutic purposes.

The active ingredient in the above procedure may be replaced by any other compound of formula I or a salt thereof, or a non-toxic biodegradable precursor thereof.

EXAMPLE 3 (ALL PARTS BY WEIGHT)

A mixture of spiro[pyrrolidine-3,9'-xanthene]-2,5-dione (50 parts), calcium carbonate (20 parts) and polyethyleneglycol (average molecular weight 4000) (30 parts) was vigorously stirred to obtain a uniform powdered form. This material was then charged into gelatine capsules using a conventional procedure such that each capsule contained 10, 20, 50 or 100 mg. of active ingredient suitable for oral administration for therapeutic purposes.

The active ingredient in the above procedure may be replaced by any other compound of formula I or a salt or non-toxic biodegradable precursor thereof.

What is claimed is:

1. A compound of the formula:

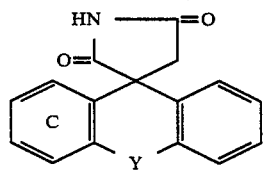

II wherein benzene ring c optionally bears a fluoro, chloro, bromo, methyl or methoxy substituent in the 6'-, 7'- or 8'-position; and Y is oxygen; or a salt with a base affording a pharmaceutically acceptable cation.

2. Spiro[pyrrolidine-3,9'-xanthene]-2,5-dione.

3. A salt of a compound of formula II as claimed in claim 1 which is an alkali metal, alkaline earth metal, aluminium, ammonium or triethanolammonium salt.

4. A composition suitable for use in inhibiting the enzyme aldose reductase which comprises an effective amount of a compound of formula II, or a pharmaceutically acceptable salt thereof, as claimed in claim 1, together with a pharmaceutically acceptable diluent or carrier.

5. A method of inhibiting the enzyme aldose reductase in a warm-blooded animal requiring such treatment, which comprises administering to said animal an aldose reductase inhibitory amount of a compound of formula II or of a pharmaceutically acceptable salt thereof, as claimed in claim 1.

* * * * *